US006485940B2

(12) United States Patent
Mundt et al.

(10) Patent No.: US 6,485,940 B2
(45) Date of Patent: Nov. 26, 2002

(54) BROAD SPECTRUM INFECTIOUS BURSAL DISEASE VIRUS VACCINE

(75) Inventors: Egbert Mundt, Millienhagen (DE); Adriaan Antonius Wilhelmus Maria Loon Van, Sambeek (NL)

(73) Assignee: Akzo Nobel N.V., BM Arnhem (NL)

( * ) Notice: Subject to any disclaimer, the term of this patent is extended or adjusted under 35 U.S.C. 154(b) by 0 days.

(21) Appl. No.: 09/888,876

(22) Filed: Jun. 25, 2001

(65) Prior Publication Data

US 2002/0064532 A1 May 30, 2002

(30) Foreign Application Priority Data

Jul. 7, 2000 (EP) .............................................. 00202430
Mar. 22, 2001 (EP) .............................................. 01201064

(51) Int. Cl.$^7$ ........................... C12P 21/06; C12Q 1/70; A61K 39/00; A61K 39/12; C07H 21/04
(52) U.S. Cl. ..................... 435/69.1; 435/5; 424/184.1; 424/204.1; 536/23.72
(58) Field of Search ................................. 435/5, 6, 69.1; 424/184.1, 204.1; 536/23.72

(56) References Cited

FOREIGN PATENT DOCUMENTS

| WO | WO 91 16925 A | 11/1991 |
|---|---|---|
| WO | WO 95 26196 A | 10/1995 |
| WO | WO 00 12677 A | 3/2000 |

OTHER PUBLICATIONS

Mundt, E.: "Tissue Culture Infectivity of Different Strains of Infectious Bursal Disease Virus Is Determined By Distinct Amino Acids in VP2", Journal of General Virology, vol. 80, 1999, pp. 2067–2076, Reading., GB.

*Primary Examiner*—Hankyel T. Park
(74) *Attorney, Agent, or Firm*—William P. Ramey, III (57) ABSTRACT

The present invention provides a broad spectrum IBDV vaccine that is able to induce a protective immune response against classical- and variant E IBDV strains. Moreover, the vaccine can be administered to poultry by mass application routes.

15 Claims, 2 Drawing Sheets

SEQUENCE LISTING

<160> NUMBER OF SEQ ID NOS: 6

<210> SEQ ID NO 1
<211> LENGTH: 1078
<212> TYPE: DNA
<213> ORGANISM: Infectious bursal disease virus
<220> FEATURE:
<221> NAME/KEY: CDS
<222> LOCATION: (1)..(1077)
<223> OTHER INFORMATION: IDENTICAL TO NUCLEOTIDES 647-1725 OF E/DEL
      SEGMENT A

<400> SEQUENCE: 1

| | | | | | | | | | | | | | | | | |
|---|---|---|---|---|---|---|---|---|---|---|---|---|---|---|---|---|
| tat | gat | ctt | ggg | tat | gtg | agg | ctt | ggt | gac | ccc | ata | ccc | gct | ata | ggg | 48 |
| Tyr | Asp | Leu | Gly | Tyr | Val | Arg | Leu | Gly | Asp | Pro | Ile | Pro | Ala | Ile | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctt | gac | cca | aaa | atg | gta | gca | aca | tgt | gac | agc | agt | gac | agg | ccc | aga | 96 |
| Leu | Asp | Pro | Lys | Met | Val | Ala | Thr | Cys | Asp | Ser | Ser | Asp | Arg | Pro | Arg | |
| | | | 20 | | | | | 25 | | | | | 30 | | | |

| | | | | | | | | | | | | | | | | |
|---|---|---|---|---|---|---|---|---|---|---|---|---|---|---|---|---|
| gtc | tac | acc | ata | act | gca | gcc | gat | aat | tac | caa | ttc | tca | tca | cag | tac | 144 |
| Val | Tyr | Thr | Ile | Thr | Ala | Ala | Asp | Asn | Tyr | Gln | Phe | Ser | Ser | Gln | Tyr | |
| | | 35 | | | | | 40 | | | | | 45 | | | | |

| | | | | | | | | | | | | | | | | |
|---|---|---|---|---|---|---|---|---|---|---|---|---|---|---|---|---|
| caa | aca | ggt | ggg | gta | aca | atc | aca | ctg | ttc | tca | gcc | aac | att | gat | gcc | 192 |
| Gln | Thr | Gly | Gly | Val | Thr | Ile | Thr | Leu | Phe | Ser | Ala | Asn | Ile | Asp | Ala | |
| | 50 | | | | | 55 | | | | | 60 | | | | | |

| | | | | | | | | | | | | | | | | |
|---|---|---|---|---|---|---|---|---|---|---|---|---|---|---|---|---|
| atc | aca | agt | ctc | agc | gtt | ggg | gga | gag | ctc | gtg | ttc | aaa | aca | agc | gtc | 240 |
| Ile | Thr | Ser | Leu | Ser | Val | Gly | Gly | Glu | Leu | Val | Phe | Lys | Thr | Ser | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| caa | agc | ctt | gta | ctg | ggc | gcc | acc | atc | tac | ctt | ata | ggc | ttt | gat | ggg | 288 |
| Gln | Ser | Leu | Val | Leu | Gly | Ala | Thr | Ile | Tyr | Leu | Ile | Gly | Phe | Asp | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| act | gcg | gta | atc | acc | aga | gct | gtg | gcc | gca | aac | aat | ggg | ctg | acg | gcc | 336 |
| Thr | Ala | Val | Ile | Thr | Arg | Ala | Val | Ala | Ala | Asn | Asn | Gly | Leu | Thr | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| ggc | atc | gac | aat | ctt | atg | cca | ttc | aat | ctt | gtg | att | cca | acc | aat | gag | 384 |
| Gly | Ile | Asp | Asn | Leu | Met | Pro | Phe | Asn | Leu | Val | Ile | Pro | Thr | Asn | Glu | |
| | | 115 | | | | | 120 | | | | | 125 | | | | |

| | | | | | | | | | | | | | | | | |
|---|---|---|---|---|---|---|---|---|---|---|---|---|---|---|---|---|
| ata | acc | cag | cca | atc | aca | tcc | atc | aaa | ctg | gag | ata | gtg | acc | tcc | aaa | 432 |
| Ile | Thr | Gln | Pro | Ile | Thr | Ser | Ile | Lys | Leu | Glu | Ile | Val | Thr | Ser | Lys | |
| | 130 | | | | | 135 | | | | | 140 | | | | | |

| | | | | | | | | | | | | | | | | |
|---|---|---|---|---|---|---|---|---|---|---|---|---|---|---|---|---|
| agt | gat | ggt | cag | gca | ggg | gaa | cag | atg | tca | tgg | tcg | gca | agt | ggg | agc | 480 |
| Ser | Asp | Gly | Gln | Ala | Gly | Glu | Gln | Met | Ser | Trp | Ser | Ala | Ser | Gly | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cta | gca | gtg | acg | atc | cat | ggt | ggc | aac | tat | cca | gga | gcc | ctc | cgt | ccc | 528 |
| Leu | Ala | Val | Thr | Ile | His | Gly | Gly | Asn | Tyr | Pro | Gly | Ala | Leu | Arg | Pro | |
| | | | | 165 | | | | | 170 | | | | | 175 | | |

| | | | | | | | | | | | | | | | | |
|---|---|---|---|---|---|---|---|---|---|---|---|---|---|---|---|---|
| gtc | aca | cta | gta | gcc | tac | gaa | aga | gtg | gca | aca | ggc | tct | gtc | gtt | acg | 576 |
| Val | Thr | Leu | Val | Ala | Tyr | Glu | Arg | Val | Ala | Thr | Gly | Ser | Val | Val | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| gtc | aca | cta | gta | gcc | tac | gaa | aga | gtg | gca | aca | gga | tct | gtc | gtt | acg | 624 |
| Val | Thr | Leu | Val | Ala | Tyr | Glu | Arg | Val | Ala | Thr | Gly | Ser | Val | Val | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| aag | acc | ctg | gtt | aca | gaa | tac | ggc | cga | ttt | gac | cca | gga | gcc | atg | aac | 672 |
| Lys | Thr | Leu | Val | Thr | Glu | Tyr | Gly | Arg | Phe | Asp | Pro | Gly | Ala | Met | Asn | |
| | 210 | | | | | 215 | | | | | 220 | | | | | |

| | | | | | | | | | | | | | | | | |
|---|---|---|---|---|---|---|---|---|---|---|---|---|---|---|---|---|
| tac | acg | aaa | ttg | ata | ctg | agt | gag | agg | gac | cac | ctt | ggc | atc | aag | acc | 720 |
| Tyr | Thr | Lys | Leu | Ile | Leu | Ser | Glu | Arg | Asp | His | Leu | Gly | Ile | Lys | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gtc | tgg | cca | aca | agg | gag | tac | act | gac | ttt | cgt | gag | tac | ttc | atg | gag | 768 |
| Val | Trp | Pro | Thr | Arg | Glu | Tyr | Thr | Asp | Phe | Arg | Glu | Tyr | Phe | Met | Glu | |

-continued

```
                     245                 250                 255
gtg gcc gac ctc aac tct ccc ctg aag att gca gga gca ttt ggc ttc      816
Val Ala Asp Leu Asn Ser Pro Leu Lys Ile Ala Gly Ala Phe Gly Phe
            260                 265                 270 aaa gac ata atc cgg gcc ata agg agg ata gct gta ccg gtg gtc tct      864
Lys Asp Ile Ile Arg Ala Ile Arg Arg Ile Ala Val Pro Val Val Ser
            275                 280                 285 aca ttg ttc cca cct gcc gct cct cta gcc cat gca att ggg gaa ggt      912
Thr Leu Phe Pro Pro Ala Ala Pro Leu Ala His Ala Ile Gly Glu Gly
            290                 295                 300 gta gac tac cta ctg ggc gat gag gca cag gct gct tca gga acc gct      960
Val Asp Tyr Leu Leu Gly Asp Glu Ala Gln Ala Ala Ser Gly Thr Ala
305                 310                 315                 320 cga gcc gcg tca gga aaa gca agg gct gcc tca ggc cgc ata agg cag     1008
Arg Ala Ala Ser Gly Lys Ala Arg Ala Ala Ser Gly Arg Ile Arg Gln
            325                 330                 335 ctg act ctc gcc gcc gac aag ggg tac gag gta gtc gcg aat cta ttc     1056
Leu Thr Leu Ala Ala Asp Lys Gly Tyr Glu Val Val Ala Asn Leu Phe
            340                 345                 350 cag gtg ccc cag aat ccc gta g                                       1078
Gln Val Pro Gln Asn Pro Val
            355
```

<210> SEQ ID NO 2
<211> LENGTH: 359
<212> TYPE: PRT
<213> ORGANISM: Infectious bursal disease virus

<400> SEQUENCE: 2

```
Tyr Asp Leu Gly Tyr Val Arg Leu Gly Asp Pro Ile Pro Ala Ile Gly
 1               5                  10                  15

Leu Asp Pro Lys Met Val Ala Thr Cys Asp Ser Ser Asp Arg Pro Arg
             20                  25                  30

Val Tyr Thr Ile Thr Ala Ala Asp Asn Tyr Gln Phe Ser Ser Gln Tyr
         35                  40                  45

Gln Thr Gly Gly Val Thr Ile Thr Leu Phe Ser Ala Asn Ile Asp Ala
     50                  55                  60

Ile Thr Ser Leu Ser Val Gly Gly Glu Leu Val Phe Lys Thr Ser Val
 65                  70                  75                  80

Gln Ser Leu Val Leu Gly Ala Thr Ile Tyr Leu Ile Gly Phe Asp Gly
                 85                  90                  95

Thr Ala Val Ile Thr Arg Ala Val Ala Ala Asn Asn Gly Leu Thr Ala
            100                 105                 110

Gly Ile Asp Asn Leu Met Pro Phe Asn Leu Val Ile Pro Thr Asn Glu
        115                 120                 125

Ile Thr Gln Pro Ile Thr Ser Ile Lys Leu Glu Ile Val Thr Ser Lys
    130                 135                 140

Ser Asp Gly Gln Ala Gly Glu Gln Met Ser Trp Ser Ala Ser Gly Ser
145                 150                 155                 160

Leu Ala Val Thr Ile His Gly Gly Asn Tyr Pro Gly Ala Leu Arg Pro
                165                 170                 175

Val Thr Leu Val Ala Tyr Glu Arg Val Ala Thr Gly Ser Val Val Thr
            180                 185                 190

Val Thr Leu Val Ala Tyr Glu Arg Val Ala Thr Gly Ser Val Val Thr
        195                 200                 205

Lys Thr Leu Val Thr Glu Tyr Gly Arg Phe Asp Pro Gly Ala Met Asn
    210                 215                 220
```

```
Tyr Thr Lys Leu Ile Leu Ser Glu Arg Asp His Leu Gly Ile Lys Thr
225                 230                 235                 240

Val Trp Pro Thr Arg Glu Tyr Thr Asp Phe Arg Glu Tyr Phe Met Glu
                245                 250                 255

Val Ala Asp Leu Asn Ser Pro Leu Lys Ile Ala Gly Ala Phe Gly Phe
            260                 265                 270

Lys Asp Ile Ile Arg Ala Ile Arg Arg Ile Ala Val Pro Val Val Ser
        275                 280                 285

Thr Leu Phe Pro Pro Ala Ala Pro Leu Ala His Ala Ile Gly Glu Gly
    290                 295                 300

Val Asp Tyr Leu Leu Gly Asp Glu Ala Gln Ala Ser Gly Thr Ala
305                 310                 315                 320

Arg Ala Ala Ser Gly Lys Ala Arg Ala Ala Ser Gly Arg Ile Arg Gln
                325                 330                 335

Leu Thr Leu Ala Ala Asp Lys Gly Tyr Glu Val Val Ala Asn Leu Phe
            340                 345                 350

Gln Val Pro Gln Asn Pro Val
        355
```

<210> SEQ ID NO 3
<211> LENGTH: 101
<212> TYPE: DNA
<213> ORGANISM: Infectious bursal disease virus
<220> FEATURE:
<221> NAME/KEY: CDS
<222> LOCATION: (3)..(101)
<223> OTHER INFORMATION: D78 VP2 CODING REGION NUCLEOTIDES 884-985

<400> SEQUENCE: 3

```
tc cac ggc ctt gta ctg ggc gcc acc atc tac ctc ata ggc ttt gat        47
   His Gly Leu Val Leu Gly Ala Thr Ile Tyr Leu Ile Gly Phe Asp
    1               5                  10                  15 ggg aca acg gta atc acc agg gct gtg gcc gca aac aat ggg ctg acg      95
Gly Thr Thr Val Ile Thr Arg Ala Val Ala Ala Asn Asn Gly Leu Thr
                20                  25                  30 acc ggc                                                              101
Thr Gly
```

<210> SEQ ID NO 4
<211> LENGTH: 33
<212> TYPE: PRT
<213> ORGANISM: Infectious bursal disease virus

<400> SEQUENCE: 4

```
His Gly Leu Val Leu Gly Ala Thr Ile Tyr Leu Ile Gly Phe Asp Gly
 1               5                  10                  15

Thr Thr Val Ile Thr Arg Ala Val Ala Ala Asn Asn Gly Leu Thr Thr
                20                  25                  30

Gly
```

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence:
    OLIGONUCLEOTIDE PRIMER

<400> SEQUENCE: 5

```
gccggtcgtc agcccattgt ttgcggccac agccctggtg attac                    45
```

```
<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence:
      OLIGONUCLEOTIDE PRIMER

<400> SEQUENCE: 6
taccgttgtc ccatcaaagc ctatgaggta gatggtggcg cccagtacaa ggccgtggac    60
```

BROAD SPECTRUM INFECTIOUS BURSAL DISEASE VIRUS VACCINE

The present invention is concerned with an IBDV mutant comprising the nucleotide sequences encoding a variant E VP2 protein in segment A of the viral genome and that is capable to infect and replicate in CEF tissue culture, a vaccine comprising this mutant and the use of this mutant for the manufacture of a vaccine.

Infectious bursal disease virus (IBDV) is a member of the Birnaviridae family. Viruses in this family have a very similar genomic organisation and a similar replication cycle. The genomes of these viruses consist of 2 segments (A and B) of double-stranded (ds) RNA. The larger segment A encodes a polyprotein, which is cleaved by autoproteolysis to form mature viral proteins VP2, VP3 and VP4. VP2 and VP3 are the major structural proteins of the virion. VP2 is the major host-protective immunogen of birnaviruses, and contains the antigenic regions responsible for the induction of neutralising antibodies. The VP4 protein is the virus-coded protease that is involved in the processing of a precursor polyprotein of the VP2, VP3 and VP4 proteins. The larger segment A possesses also a second open reading frame (ORF), preceding and partially overlapping the polyprotein gene. This second open reading frame encodes a protein VP5 of unknown function that is present in IBDV infected cells. The smaller segment B encodes VP1, a 90 kDa multifunctional protein with polymerase and capping enzyme activities.

For IBDV, two serotypes exist, serotype 1 and 2. The two serotypes may be differentiated by virus neutralisation (VN) tests. Furthermore, subtypes of serotype 1 have been isolated. These so-called "variant" viruses of serotype 1 can be identified by cross-neutralisation tests, a panel of monoclonal antibodies or RT-PCR. These subtypes of serotype 1 of IBDV have also been described in literature, for example: classical, variant-E, GLS, RS593 and DS326 strains (Van Loon, et al. Proceedings of the International symposium on infectious bursal disease and chicken infectious anaemia, Rauischholzhausen, Germany, 179–187, 1994).

Infectious Bursal disease (IBD), also called Gumboro disease, is an acute, highly-contagious viral infection in chickens that has lymphoid tissue as its primary target with a selective tropism for cells of the bursa of Fabricius. The morbidity rate in susceptible flocks is high, with rapid weight loss and moderate mortality rates. Chicks that recover from the disease may have immune deficiencies because of the destruction of the bursa of Fabricius, which is essential to the defence mechanism of the chicken. The IBD-virus causes severe immunosuppression in chickens younger than 3 weeks of age and induces bursal lesions in chicks up to 3 months old.

For many years the disease could be prevented by inducing high levels of antibodies in breeder flocks by the application of an inactivated vaccine, to chickens that had been primed with attenuated live IBDV vaccine. This has kept economic losses caused by IBD to a minimum. Maternal antibodies in chickens derived from vaccinated breeders prevent early infection with IBDV and diminish problems associated with immunosuppression. In addition, attenuated live vaccines have also been used successfully in commercial chicken flocks after maternal antibodies had declined.

Recently, very virulent strains of IBDV have caused outbreaks of disease with high mortality in Europe. The current vaccination programs failed to protect chicks sufficiently. Vaccination failures were mainly due to the inability of live vaccines to infect the birds before challenge with virulent field virus.

A further cause of acute disease in vaccinated flocks is the emerging of antigenic variants in the mid-1980s, in particular in the USA. The most important new antigenic subtypes of serotype 1 IBDVs were the Delaware variant E and GLS strains. Until then, vaccines used were based on live attenuated or killed IBDV strains of the classical type only. However, despite the fact that classical IBDV vaccine strains induce a certain degree of cross-protection against infection of chickens by other subtype strains (and vice-versa), substantial economic losses have been sustained as a result of vaccination with vaccines based on only one of the subtype viruses.

As a result of these developments in the field it became necessary to incorporate both classical and variant IBDV subtype vaccine strains into the IBDV vaccines to obtain a broad spectrum protection.

As described above, both live and killed vaccines based on classical strains are generally used in the field. The killed classical vaccines are commonly administered per injection, whereas the live classical vaccines are administered per injection or by one of the inexpensive, mass application techniques, such as spray-, aerosol and drinking water vaccination.

Delaware variant E viruses identified so far are highly virulent and can be administered as an inactivated vaccine only. Until now, there has been only one successful attempt to adapt and attenuate a variant E strain in cell culture. This vaccine strain designated as 89/03 is able to induce protection against variant E infection, but has the disadvantage that it does not take if administered by one of the mass application routes. This vaccine virus needs to be administered by injection, subcutaneously or intramuscularly (Hein et al., Proceedings of the 43th Western poultry disease conference, pages 102–103, 1994, Sacramento, USA).

For protecting birds against infection by IBDV of the GLS subtype, only inactivated vaccines are available.

Mundt (J. Gen. Virology 80, 2067–2076, 1999) identified the structural requirements at the molecular level which allows IBDV strains that were only able to infect and replicate in vivo in the bursa of Fabricius, to infect and replicate in chicken embryo fibroblast (CEF) tissue culture as well. Two amino acid exchanges in the VP2 protein at positions 253 (Gln to His) and 284 (Ala to Thr) were necessary and sufficient for the ability of IBDV bursa strains (BU) to infect CEF and other tissue cultures. In particular, two chimeric D78/variant E IBDV mutants with a tissue culture (TC) phenotype are disclosed in this document.

In view of the above, a need existed for a live attenuated Delaware variant E IBDV vaccine that is efficacious if administered via a mass application route. Furthermore, a need existed to obtain a broad spectrum IBDV vaccine strain that affords adequate protection against IBDV strains of two or more subtypes. Such a broad spectrum vaccine prevents that separate vaccine viruses for each IBDV subtypes have to be manufactured and formulated into a combination vaccine.

It is an object of the present invention to provide an IBDV mutant that is able to induce a protective immunity in chickens against virulent strains of at least two IBDV subtypes. It is a further object to provide an IBDV mutant which affords protection against virulent IBDV variant E strains and that at the same time can be administered via a mass application technique commonly used for live IBDV vaccination.

It has been found now that these objects have been met by providing an IBDV mutant comprising the nucleotide sequences encoding a variant E VP2 protein in segment A of the viral genome and that is capable to infect and replicate in CEF tissue culture, characterised in that the mutant comprises one or more mutations in the variant E VP2 coding region such that, (i) the codon for the amino acid at position 254 encodes Glycine, and/or (ii) the codon for the amino acid at position 270 encodes Threonine.

It has been shown by the present inventors that the chimeric IBDV D78/variant E bursa (BU) mutant disclosed in Mundt et al. (1999, supra), displaying the culture (BU) and immunogenicity characteristics of a variant E strain, is virulent and induces complete lymphocyte depletion after administration to chickens. Furthermore, it is shown in Example 2 that the corresponding tissue culture (TC) mutant of this strain is less virulent and is able to induce a partial protective immune response if administered per injection. However, at the same time the TC mutant induces only poor protection against challenge if this mutant is administered via the ocular route (a route that is a model for drinking water administration). Surprisingly, the inventors have identified that further mutations in the naturally occurring codons for amino acids 254(Ser) and/or 270(Ala) in the VP2 gene of variant E viruses, resulting in codons encoding amino acid 254(Gly) and/or 270(Thr), provide a live attenuated IBDV mutant that:

(i) is able to induce virus neutralising (VN) antibody titers against classical- and variant E subtype IBDV strains of about the same level, (ii) is able to induce protection in vaccinated animals against challenge with virulent classical- and variant E subtype IBDV strains, (iii) is able to induce protection if administered via a mass application route.

IBDV subtypes are well defined in the art, e.g. by means of their reaction pattern with monoclonal antibodies. An IBDV of the variant E subtype specifically reacts with virus neutralising Moab 67 that has been deposited at the ATCC by Dave Snyder on Sep. 14, 1992, under accession no. HB 11122 (see also, Vakharia et al., Virus Research 31, 265–273, 1994).

The mutations resulting in an IBDV mutant according to the invention are introduced in the coding region for the variant E VP2 protein at the codons for amino acid 254(Ser) and/or 270(Ala).

An advantageous IBDV mutant according to the invention comprises the desired mutations in both codons or in the codon for amino acid 254.

Figure 1:
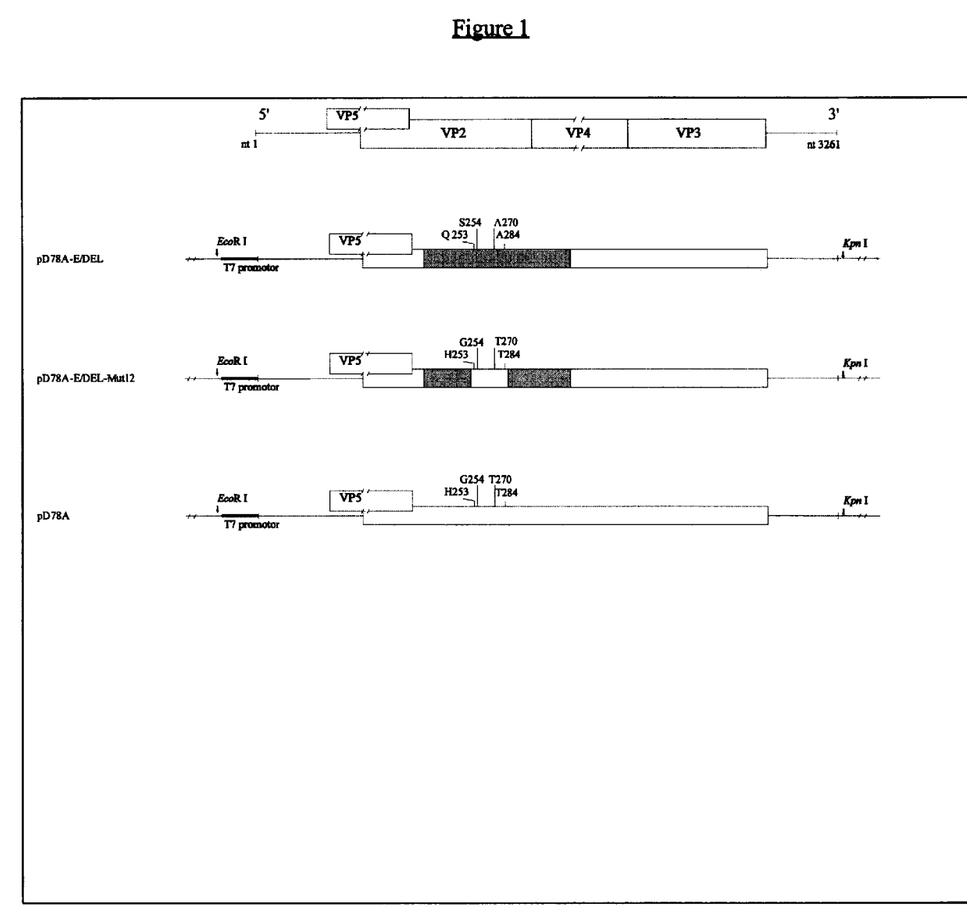

The exchange of nucleotide 890 (A to G) and 938 (G to A) lead to the substitutions of amino acid 254 (Ser to Gly) and 270 (Ala to Thr), respectively. As described above, the genomic organisation of IBD viruses is well established: the IBDV genome comprises a large segment A and a smaller segment B. The segment A of IBDV comprises a large open reading frame (ORF) encoding a polyprotein of about 110 kDa (VP2-VP4-VP3; FIG. 1). The complete nucleotide sequences of the segment A and segment B of many IBDV strains have been determined. Furthermore, the location within the ORF, the nucleotide sequence encoding the variant E VP2 protein and the amino acid sequence of the variant E VP2 protein have been determined by Vakharia et al., Avian Diseases 36, 736–743, 1992; Vakharia et al., Virus Res. 31, 265–273, 1994; Heine et al., J. Gen. Virol. 22, 1835–1843, 1991. Additionally, the nucleotide sequence of the DNA fragment comprising variant E VP2 coding sequences (nucleotides 647–1725) and corresponding to amino acid sequences 172–532 of the polyprotein used for generating an IBDV mutant according to the invention as described in the Examples are shown in SEQ ID. No. 1 and 2.

The numbers used herein to indicate the amino acid positions refer to numbering of the amino acids in the IBDV polyprotein as commonly used in the art. The numbers indicating the nucleotide positions are based on the complete nucleotide sequence of the segment A of the IBDV genome as described by Mundt and Müller (J. Gen. Virol. 77, 437–443, 1995; NCBI accession number X 84034).

It is demonstrated in Mundt (1999, supra) that the prerequisite for an IBDV strain with a classical- or variant E phenotype to infect and replicate in CEF tissue culture is the presence of codons encoding amino acid 253(His) and 284(Thr) in the VP2 gene of the respective strains. Therefore, in particular, an IBDV strain according to the present invention displaying the property to infect and replicate in CEF tissue culture comprises amino acid 253 (His) and 284(Thr). Such an IBDV strain can be obtained by the methods disclosed in Mundt (1999, supra). Furthermore, such a method is also described in Example 1.

As a result of the degeneracy of the genetic code various possibilities exist for the codons encoding amino acid 254 (Gly) and 270(Thr) of the polyprotein of an IBDV mutant according to the invention. The codon in the VP2 coding region for amino acid 254(Gly) may be GGA, GGC, GGG or GGT, GGC being preferred, whereas the codon for amino acid 270(Thr) may be ACT, ACC, ACA or ACG, ACG being preferred.

Variant E IBDV strains having the property (i) to infect and replicate in CEF tissue culture and (ii) to induce a broad-spectrum immune response upon administration via a mass application route, can be prepared by introducing the specific relevant codons mentioned above in a naturally occurring variant E strain.

Alternatively, this result can also be obtained by exchanging part of the variant E VP2 coding region by a corresponding part of the genomic sequence of a known (classical) IBDV strain that already comprises the desired codons at the relevant positions. Full length genomic sequences of classical strains are disclosed in U.S. Pat. No. 5,871,744 (Vakharia and Mundt) and EP patent application no. 98201704.8 (Akzo Nobel NV).

In particular, an IBDV mutant according to the invention is provided that comprises part of the VP2 coding sequence of the classical strain D78 encoding a VP2 protein fragment that comprises amino acid positions 253–284 and having the desired codons as defined above.

A preferred IBDV mutant according to the present invention comprises part of the D78 VP2 coding region spanning nucleotide position 884–985 having a nucleotide sequence shown in SEQ ID No. 3. This nucleotide fragment replaces the corresponding fragment of the variant E VP2 coding region and encodes inter alia the following amino acids: 253(His), 254(Gly), 270(Thr) and 284(Thr) (SEQ ID No. 4).

An IBDV mutant according to the present invention may comprise the genetic backbone of the segment A of a variant E IBDV strain, including a mutated VP2 coding region as described above. However, an IBDV mutant according to the invention can also be based on the genetic backbone of another IBDV strain, such as a classical- or GLS strain, a classical strain, more in particular strain D78, being preferred.

In such a "chimeric" IBDV mutant, VP2 coding sequences on the genetic backbone of segment A of a first type of IBDV strain are replaced by the corresponding, relevant variant E VP2 coding sequences that additionally comprise the desired mutations that are responsible for the advantageous properties of the new IBDV mutant.

The VP2 coding sequences encoding a variant E VP2 protein may comprise the (mutated) genetic information encoding the complete variant E VP2 protein (nucleotide positions 131–1666) or may comprise a fragment thereof that encodes a VP2 protein that is able to induce variant E virus neutralising antibodies. In the latter case the variant E VP2 coding sequences may be complemented with VP2 coding sequences of another IBDV subtype such that the IBDV mutant expresses a complete VP2 protein.

In particular, such an IBDV mutant may comprise at least a (mutated) variant E VP2 coding fragment spanning the so-called variable region of the VP2 gene. Bayliss et al. (J. Gen. Virol. 71, 1303–1312, 1990) determined this region to be located within the nucleotide positions 745–1182.

Preferably, the IBDV mutant comprises the variant E VP2 coding sequences spanning nucleotides 647–1666, including the desired mutations described above.

The generation of the (chimeric) IBDV mutants can be achieved by means of the recently established infectious cRNA system for IBDV (Mundt and Vakharia, Proc. Natl. Acad. Sci. USA 93, 11131–11136, 1996). This reverse genetics system opens the possibility to introduce mutations in the RNA genome of the IBDV. The most important step in this reverse genetics system is to provide full length cDNA clones of the segments A and B of IBD virus, including the nucleotides of the 5'- and 3'- ends of both these segments. After cloning procedures, the full length sequences of segment A and B are operably linked to a promoter which is able to bind a DNA dependent RNA polymerase, such as the T7, SP6 or T3 polymerase, the T7 promoter being preferred. The DNA dependent polymerase is able to describe viral cRNA from full length cDNA clones of segment A and B, respectively. This cRNA is able to induce replication of the virus and the isolation of viable virus. This procedure can be performed with every natural occurring IBDV.

Reverse genetics systems have been described for various IBDV strains, such as D78 (Yao et al., J. Virol. 72, 2647–2657, 1998), strain HK46 (Lim et al., J. Virol. 73, 2854–2862, 1999) and CEF 94 (Boot et al., Virology 265, 330–341, 1999).

The segment B of an IBDV mutant according to the invention can be derived from any IBDV strain, preferably from a classical IBDV strain, most preferably from strain D78 or P2 (U.S. Pat. No. 5,871,744 and EP patent application no. 98201704.8).

IBDV mutants as described above comprising segment B of strain P2 display particular advantageous attenuated and protective properties, especially a mutant having amino 254(Gly) or 254(Gly)/270(Thr).

The desired mutations can be introduced into the IBDV genome by means of methods generally known in the art for this purpose. In particular, the mutation(s) are introduced by means of site-directed mutagenises. Methods for introducing a mutation in the IBDV genome are described herein, but are also generally used in the art (Mundt and Vakharia, 1996, supra; Yao et al., J. Virology 72, 2647–2654, 1998; Mundt et al., 1999, supra; EP patent application no. 98201704.8; Current Protocols in Molecular Biology, eds.: F. M. Ausubel et al., Wiley N.Y., 1995 edition, pages 8.5.1.–8.5.9.and Kunkel et al. in Methods in Enzymology vol. 154, 376–382, 1987).

As demonstrated in the Examples, an IBDV mutant according to the invention displays very favourable properties that can lead to a new type of IBDV vaccine. Therefore, another aspect of this invention is a vaccine for use in the protection of poultry against disease resulting from IBDV infection. The vaccine comprises an IBDV mutant as defined above, together with a pharmaceutical acceptable carrier or diluent.

The IBDV mutant can be incorporated into the vaccine as live attenuated or inactivated virus, however, the live form is preferred because this allows the use of all the advantageous properties of the IBDV mutants of the present invention.

A vaccine according to the invention can be prepared by conventional methods such as for example commonly used for the commercially available live- and inactivated IBDV vaccines. Briefly, a susceptible substrate is inoculated with an IBDV mutant according to the invention and propagated until the virus replicated to a desired infectious titre after which IBDV containing material is harvested.

Every substrate which is able to support the replication of IBDV mutants can be used to prepare the vaccine according to the present invention, including primary (avian) cell cultures, such as chicken embryo fibroblast cells (CEF) or chicken embryo liver cells (CEL), mammalian cell lines such as the VERO cell line or the BGM-70 cell line, or avian cell lines such as QT-35, QM-7 or LMH. Usually, after inoculation of the cells, the virus is propagated for 3–10 days, after which the cell culture supernatant is harvested, and if desired filtered or centrifuged in order to remove cell debris.

Alternatively, the IBDV mutant is propagated in embryonated chicken eggs. In particular, the substrate on which these IBDVs are propagated are SPF embryonated eggs. Embryonated eggs can be inoculated with, for example 0.2 ml IBDV mutant containing suspension or homogenate comprising at least $10^2$ TCID$_{50}$ per egg, and subsequently incubated at 37° C. After about 2–5 days the IBD virus product can be harvested by collecting the embryo's and/or the membranes and/or the allantoic fluid followed by appropriate homogenising of this material. The homogenate can be centrifuged thereafter for 10 min at 2500×g followed by filtering the supernatant through a filter (100 $\mu$m).

The vaccine according to the invention containing the live virus can be prepared and marketed in the form of a suspension or in a lyophilised form and additionally contains a pharmaceutically acceptable carrier or diluent customary used for such compositions. Carriers include stabilisers, preservatives and buffers. Suitable stabilisers are, for example SPGA, carbohydrates (such as sorbitol, mannitol, starch, sucrose, dextran, glutamate or glucose), proteins (such as dried milk serum, albumin or casein) or degradation products thereof. Suitable buffers are for example alkali metal phosphates. Suitable preservatives are thimerosal, merthiolate and gentamicin. Diluents include water, aqueous buffer (such as buffered saline), alcohols and polyols (such as glycerol).

If desired, the live vaccines according to the invention may contain an adjuvant. Examples of suitable compounds and compositions with adjuvant activity are the same as mentioned below.

Although administration by injection, e.g. intramuscularly, subcutaneously or in ovo of the live vaccine according to the present invention is possible, the vaccine is preferably administered by an inexpensive mass application route commonly used for IBDV vaccination. For IBDV vaccination this route includes drinking water, spray and aerosol vaccination.

For administration by the drinking water route it is customary to deprive the animals of water for about 2 to 4 hours before placing the vaccine containing water in front of them, and it is important that there is enough drinker space for all birds to drink evenly. The vaccine is applied in fresh drinking water at a concentration calculated to give each bird a sufficient dose.

In order to prevent a dramatic reduction of the viable vaccine virus by the presence of small amounts of chlorine, iron, zinc or copper ions in the drinking water, preferably a protectant such as skim milk (powder) is added to the water containing vaccine.

The spray method, comprising the coarse spray and aerosol administration, involves the administration of the live IBDV vaccine incorporated in small liquid particles. In the coarse spray method particles usually have an initial droplet size ranging from 10 to 100 microns and in the aerosol administration method droplets usually range from <1 to 50 microns.

In order to prevent inactivation of the live vaccine virus because of increased concentration of dissolved salts as a result of desiccation of the (tap) water particles, small amounts of a protein protectant, such as skimmed milk, skimmed milk powder or gelatin can be added to aqueous phase.

For the generation of the small particles, conventional spray-apparatus and aerosol generators can be used, such as the commercially available spray generators for knapsack spray, hatchery spray and atomist spray. Also the drinking water vaccination can be carried out using conventional apparatus. Details concerning conventional spray/aerosol- and drinking water vaccination can be found in the "Compendium, administration of poultry vaccines" issued by the Gezondheidsdienst voor Pluimvee, Doorn, The Netherlands, van Eck et al., VI–VII, 1988.

In another aspect of the present invention a vaccine is provided comprising the IBDV mutant in an inactivated form. The major advantage of an inactivated vaccine is the high levels of protective antibodies of long duration that can be achieved against both classical and variant E IBDV strains.

The aim of inactivation of the viruses harvested after the propagation step is to eliminate reproduction of the viruses. In general, this can be achieved by chemical or physical means well known in the art.

A vaccine containing the inactivated IBDV mutant can, for example comprise one or more of the above-mentioned pharmaceutically acceptable carriers or diluents suited for this purpose.

Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol F® or Marcol 52® or a vegetable oil such as vitamin E acetate, and saponins.

The vaccine according to the invention comprises an effective dosage of the IBDV mutant as the active component, i.e. an amount of immunising IBDV material that will induce immunity in the vaccinated birds against challenge by a virulent virus. Immunity is defined herein as the induction of a significant higher level of protection in a population of birds after vaccination compared to an unvaccinated group.

Typically, the live vaccine according to the invention can be administered in a dose of $10^{2-10.9}$ TCID$_{50}$ infectious dose$_{50}$ (TCID$_{50}$) per animal, preferably in a dose ranging from $10^{4.0-10^{7.0}}$ TCID$_{50}$. Inactivated vaccines may contain the antigenic equivalent of $10^{5-10.9}$ TCID$_{50}$ per animal.

Inactivated vaccines are usually administered parenterally, e.g. intramuscularly or subcutaneously.

Although, the IBDV vaccine according to the present invention may be used effectively in chickens, also other poultry such as turkeys, guinea fowl and partridges may be successfully vaccinated with the vaccine. Chickens include broilers, reproduction stock and laying stock.

The age of the animals receiving a live or inactivated vaccine according to the invention is the same as that of the animals receiving the conventional live- or inactivated IBDV vaccines. For example, broilers (free of maternally derived antibodies-MDA) may be vaccinated at one-day-old or in ovo, whereas broilers with high levels of MDA are preferably vaccinated at 2–3 weeks of age. Laying stock or reproduction stock with low levels of MDA may be vaccinated at 1–10 days of age followed by booster vaccinations with inactivated vaccine on 6–12 and 16–20 weeks of age.

The invention also includes combination vaccines comprising, in addition to the IBDV mutant described above, one or more immunogens derived from other pathogens infectious to poultry.

Preferably, the combination vaccine additionally comprises one or more vaccine strains of Mareks Disease virus (MDV), infectious bronchitis virus (IBV), Newcastle disease virus (NDV), egg drop syndrome (EDS) virus, turkey rhinotracheitis virus (TRTV) or reovirus.

EXAMPLES

Example 1

Generation of Broad Spectrum Classical/Variant E IBDV Mutant

Material and Methods

Virus and Cells

The serotype I strain D78 (Intervet International BV, Boxmeer, Netherlands) was propagated in chicken embryo cells (CEC). CEC derived from embryonated SPF eggs were grown in Dulbeccos minimal essential medium (DMEM) supplemented with 10% fetal calf serum (FCS) and were used for propagation of recovered virus and passaging of transfection supernatants. Transfection experiments and immunofluorescence assays were performed using quail muscle cells (QM-7, ATCC) grown in medium 199 supplemented with 10% FCS.

Contruction of a Full Length cDNA Clone of Segment B IBDV Strains

For cloning of the full length cDNA of segment B of serotype I strain D78, virus was propagated in CEC and purified by ultracentrifugation. Genomic viral RNA of strain D78 was purified, reverse transcribed into cDNA, and amplified by polymerase chain reaction (PCR) following standard procedures using oligonucleotides as described by Mundt and Vakharia (1996, supra). Amplification product was cloned blunt ended and plasmids containing appropriate PCR fragments were sequenced. The cloning procedure to obtain a plasmid containing the full length cDNA of segment B (pUC18BD78) under control of the T7- RNA polymerase promotor corresponded to the procedure described by Mundt and Vakharia (1996, supra) for segment B of strain P2.

Construction of Intergeneric IBDV Plasmids

For substitution of IBDV specific sequences a plasmid containing the complete coding region of the variant E strain E/Del was used (Vakharia, Biotechnology Annual Review 3, 151–168, 1997). pEDEL22BacII was cleaved with restriction enzymes Nde I and Sal I, nucleotides 647 and 1725 (SEQ ID No. 1), respectively, in accordance to the full length sequence of strain P2 (NCBI accession number X 84034) to obtain a 1078 bp fragment encompassing coding sequences of the variable region of VP2 (Bayliss et al., 1990, supra) and sequences of VP4 of strain E/Del. After ligation into Nde I- Sal I cleaved pD78A/ΔNB (Mundt, 1999, supra) a chimeric full length plasmid pD78A-E/Del containing sequences of segment A of strain D78 as well as E/Del was established (Mundt, 1999, supra). Plasmid pD78A-E/Del was used as basis for the site directed mutagenesis.

Figure 2:
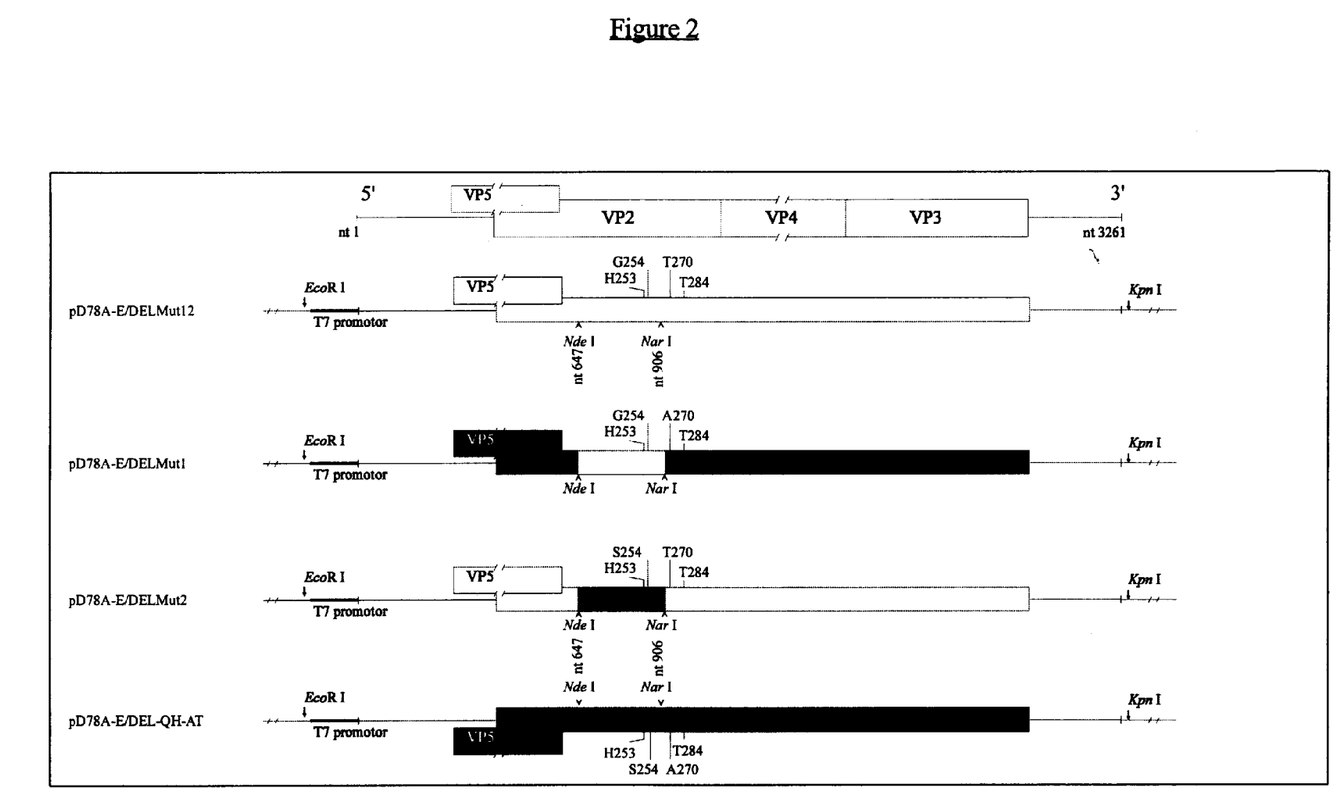

To this end pD78A-E/Del was cleaved with the restriction enzymes Sac I and Sal I, nucleotides 868 and 1725, in accordance to the full length sequence of strain P2 and cloned into an appropriate cleaved plasmid vector pBS⁻ (Stratagene) to obtain pBSD78-E/Del. The site directed mutagenesis experiments were performed as described earlier (Kunkel et al., 1992, supra). Site directed mutagenesis of the nucleotide sequence (nt 941–985) was obtained by using the oligonucleotide D78-E/Delmut12-1 (Table 1, SEQ ID No. 5) and plasmid pBSD78-E/Del. The sequence of interest was controlled by sequencing and a plasmid containing the changed sequence was used for a second mutagenesis experiment. To this end the sequence of the resulting plasmid (pBSD78-E/Delmut1) was mutagenised by using oligonucleotide D78-E/Delmut12-2 (Table 1, SEQ ID No. 6). Resulting plasmids were sequenced and a appropriate plasmid (pBSD78-E/Delmut12) was cleaved with Sac I and Spe I, nucleotides 868 and 1181, in accordance to the full length sequence of strain P2. The obtained fragment containing the mutagenised sequence was ligated into the appropriate cleaved pD78A-E/Del. The resulting plasmid pD78A-E/Delmut12 was controlled by sequencing. The plasmid contains exchanged codon for the amino acids 253, 254, 270, and 284. Here the codon for the amino acids of the E/Del-sequence were substituted with such of the D78-sequence (Q 253 H, S 254 G, A 270 T, A 284 T). Plasmids pD78A, pD78A-E/Del and pD78A-E/DelMut12 are depicted in FIG. 1. Available plasmids were used for construction of further intergeneric plasmids. To this end plasmids pD78A-E/DelMut12 as described above and pD78A-E/Del-QH-AT (Mundt, 1999, supra) were Nde I/Nar I cleaved and both DNA fragments of each plasmid were eluted. The Nde I/Nar I fragment of pD78A-E/DelMut12 was ligated into the cleaved Nde I/Nar I backbone of pD78A-E/Del-QH-AT to obtain pD78A-E/DelMut1. Using this strategy following codon for the amino acids of the E/Del- sequence were substituted with such of the D78- sequence (Q 253 H, S 254 G, A 284 T). To obtain a plasmid (pD78A-E/DelMut2) where the following codon for the amino acids of the E/Del-sequence were substituted with such of the D78-sequence (Q 253 H, A 270 T, A 284 T) the Nde I/Nar I fragment of pD78A-E/Del-QH-AT was ligated into the Nde I/Nar I backbone of pD78A-E/DelMut12. Maps of the plasmids pD78A-E/DelMut12, pD78A-E/DelMut1, pD78A-E/DelMut2, and pD78A-E/DelQH-AT are depicted in FIG. 2.

TABLE 1

Oligonucleotides used for the construction of full length cDNA clones of IBDV segment A containing amino acid substitions*

| Designation | Nucleotide sequence | Orientation | Amino acid substitution | Nucleotide no. |
| --- | --- | --- | --- | --- |
| D78-E/Delmut12-1 | GCCGGtCGTCAGCCCATTGTTTGCGGCCACAGCcCTGGTGATTAC | Antisense | A284T | 941–985 |
| D78-E/Delmut12-2 | TACCGttGTCCCATCAAAGCCTATgAGGTAGATGGTGGCGCCCAGTACAAGGCcgTGGAC | Antisense | Q253H S254G A270T | 884–943 |

*Composition and location of the oligonucleotide primers used for site directed mutagenesis. Changed nucleotides for mutagenesis are in small letter code and the changed coding nucleotide triplett are highlighted in boldface type. The positions where the primers bind (nucleotide no.) and the numbering of the amino acids are in accordance to the published sequence of strain P2 (Mundt and Müller, 1995, supra).

Virus Recovery from cRNA in Tissue Culture

For in vitro transcription of RNA of plasmids containing segment A (pD78A-E/DelMut1, pD78A-E/DelMut2, pD78A-E/DelMut12) and pD78B were linearized by cleavage with either BsrGI or Pst I. Further treatment of linearized DNA and transcription were carried out as described by Mundt & Vakharia (1996, supra), with two exceptions: i) the transcription mixtures were not purified by phenol/ chloroform extraction, and ii) CEC were used for transfection experiments as described by Mundt and Vakharia (1996, supra). Two days after transfection cells were freeze/thawed, centrifuged at 700×g to eliminate cellular debris, and the resulting supernatants were further clarified by filtration through 0.45 μm filters and stored at −70° C. For immunofluorescence studies cells were grown on sterile cover slips. Mutants containing segment B of P2 were prepared as described above.

Detection of IBDV Antigen

IBDV antigen was detected by indirect immunofluorescence assay (IFA). Supernatants of transfected CEC were passaged onto CEC. For IFA CEC grown on cover slips were incubated with supernatants resulting from the passaging experiments. After 16 hours cells were acetone fixed and processed for IFA.

Results

Transfection Experiments with Chimeric cRNA

For transfection experiments full length cDNA clones of chimeric segments A (pD78A-E/DelMut1, pD78A-E/DelMut2, pD78A-E/DelMut12) were transcribed into synthetic cRNA and cotransfected with segment B (pD78B or pP2B) full length cRNA into CEC. Two days after transfection cells were freeze/thawed and the resulting supernatants were passaged once on CEC. After freeze/thawing transfection and passage supernatants were tested for IBDV antigen by IFA using CEC. Virus was generated after transfection of cRNA from plasmid pD78B or pP2B in combination with pD78A-E/DelMut1 leading to the mutant virus D78A-E/DelMut1 (classical/variant E (TC)-254(Gly)//D78B), pD78A-E/DelMut2 leading to the mutant virus D78A-E/DelMut2 (classical/variant E (TC)-270(Thr)//D78B), and pD78A-E/DelMut12 leading to the mutant virus D78A-E/DelMut12 (classical/variant E (TC)-254(Gly)/270(Thr)//D78B), and corresponding mutants comprising genomic segment B of strain P2 (Mut1//P2B, Mut2//P2B and Mut12//P2B).

Example 2

A Properties of IBDV D78/Variant E (BU) and (TC) Mutant

The biological properties of two prior art IBDV mutants D78/variant E (13U) (designated as D78A-E/Del) and D78/variant E (TC) (designated as D78A-E/Del-QH-AT-SR) disclosed in Mundt (1999, supra) were determined.

Material and Methods

The effect of the different vaccines was assessed by measurement of the resistance to challenge obtained from administering a challenge virus (virulent IBDV strain variant E), 14 days after vaccination. The vaccines investigated were the vaccines D78/variant E (BU) and (TC), and the commercial available classical vaccine Nobilis strain D78 (Intervet International BV, the Netherlands). The (BU) vaccine, $10^{2.0}$ EID$_{50}$/animal, was applied via the eye-drop route at 2 weeks of age. The (TC) vaccine, $10^{5.5}$ or $10^{3.5}$ TCID$_{50}$/animal, was applied via the eye-drop route or via intramuscular injection at 2 weeks of age, respectively. The commercial available classical vaccine Nobilis strain D78, $10^{3.3}$TCID$_{50}$/animal was applied via the eye-drop route at 2 weeks of age. Presence of IBDV in the bursa of Fabricius and microscopic lesions in the bursa of 5 animals per group were investigated, 3, 7, 10 and 13 days after vaccination and 3 days after challenge.

Protection against challenge in this experiment and the experiments described below was assessed by determining (i) acute lesions 3 days post challenge, (ii) viral antigen in the bursa 3 days post challenge and (iii) a lesion score of 5 (100% lymphocyte depletion).

Results (i) Average Microscopic Lesion Score in the Bursa 3, 7, 10 and 13 Days After Vaccination and 3 and 10 Days After Challenge As can be seen from table 2, the IBDV (BU) strain induced complete lymphocytic depletion, already 7 days after vaccination. The TC adapted IBDV strain did not induce lesions after vaccination. The commercial vaccine induces mild to moderate lesions after vaccination. Further data showed that animals vaccinated with the D78/variant E (BU) mutant or D78 were protected against challenge. However, animals vaccinated with the D78/variant E (TC) mutant via the ocular or intramusculair route developed (different levels of) acute lesions after challenge indicating that only poor and partial protection was obtained, respectively.

The control animals were not protected as all animals showed acute lesions and 100% lymphocyte depletion, 3 days after challenge.

TABLE 2

Average bursal lesion score

| Virus | Days after vaccination | | | | Days after challenge | |
|---|---|---|---|---|---|---|
| | 3 | 7 | 10 | 13 | 3 | 10 |
| D78/variant E (BU) | 3.2 | 5.0 | 5.0 | 5.0 | 4.4C | 4.7 |
| D78/variant E (TC) (oc) | 0 | 0 | 0 | 0 | 3.0A | 4.1 |
| D78/variant E (TC) (im) | 0 | 0 | 0 | 0 | 1.0A | 2.8 |
| Nobilis strain D78 | 0.2 | 2.2 | 2.0 | 1.8 | 2.8C | 1.9 |
| None vaccinated controls | | | | | 5.0A | |

(oc) = ocular route;
(im) = intramuscular route;

TABLE 2-continued

Average bursal lesion score

| Virus | Days after vaccination | | | | Days after challenge | |
|---|---|---|---|---|---|---|
| | 3 | 7 | 10 | 13 | 3 | 10 |

C = chronic lesions;
A = acute lesions (ii) Detection of IBDV with an ELISA System in the Bursa 3, 7, 10 and 13 Days After Vaccination and 3 Days After Challenge As can be seen from table 3, the D78/variant E (BU) virus could be isolated 3 and 7 days after vaccination. No virus could be detected 3 days after challenge indicating that the animals were protected against challenge. In contrast from the animals vaccinated with the tissue culture adapted strain D78/variant E (TC) we could not isolate the vaccine virus. Three days after challenge, animals vaccinated via the ocular route 4 out of 5 contained challenge virus. Three days after challenge for animals vaccinated via the intramuscular route 2 out of 5 contained challenge virus. Indicating that animals vaccinated via the ocular or intramuscular route with D78/variant E (TC) were protected for 20 or 60%, respectively. The commercial vaccine virus could be isolated 3, 7 and 10 days after vaccination. No virus could be detected 3 days after challenge indicating that the animals were protected against challenge.

All control animals has viral antigen in the bursa.

TABLE 3

Presence of IBDV in the bursa of Fabricius.

| Virus | Days after vaccination | | | | Days after challenge | |
|---|---|---|---|---|---|---|
| | 3 | 7 | 10 | 13 | 3 | % protection |
| D78/variant E (BU) | 4/5* | 5/5 | 0/5 | 0/5 | 0/5 | 100 |
| D78/variant E (TC) (oc) | 0/5 | 0/5 | 0/5 | 0/5 | 4/5 | 20 |
| D78/variant E (TC) (im) | 0/5 | 0/5 | 0/5 | 0/5 | 2/5 | 60 |
| Nobilis strain D78 | 1/5 | 2/5 | 1/5 | 0/5 | 0/5 | 100 |
| None vaccinated controls | | | | | 8/8 | 0 |

(oc) = ocular route;
(im) = intramuscular route;
*Number of positive animals with viral antigen present per total number investigated.

B Properties of the Broad Spectrum Classical/Variant E (TC) IBDV Mutant

Materials and Methods

Preparation of IBDV Vaccines

Primary chicken embryo fibroblasts (CEF) cells were prepared at a final concentration of $2 \times 10^6$/ml. The cells were cultured in Eagles minimum essential medium containing 5% fetal calf serum. To 15 ml of this cell suspension 0.1 ml IBDV-strain classical/variant E (TC)-254(Gly)/270(Thr) (=Mut12) (at passage level 2) was added. After incubation for 3–6 days in a high humidity incubator at 37° C., the supernatant (passage level 3) was taken to carry out animal experiment 1. The supernatant was diluted to result in a vaccine dose of $10^{3.0}$, $10^{4.0}$ or $10^{5.0}$ TCID$_{50}$/animal.

For the second animal experiment the IBDV strain classical/variant E (TC)-254(Gly)/270(Thr) was further purified. Three plaque purification rounds were carried out. Next the virus was cultured in the same way as described above. The ninth passage level (P9) was used in the second animal experiment. Commercially available classical IBDV vaccine Nobilis strain D78 (Intervet International BV, the Netherlands) was used in the second experiment.

Experiment 1

An animal experiment was carried out to study the safety and efficacy characteristics of the broadspectrum vaccine virus strain classical/variant E (TC)-254(Gly)/270(Thr) in 14 days old SPF birds. The vaccine virus was applied via the eye-drop or the intramuscular route. Virus was re-isolated on CEF from bursae that contained IBDV-antigen after vaccination. The efficacy of the broadspectrum vaccine classical/variant E (TC)-254(Gly)/270(Thr) was assessed by measurement of the serological response and resistance to challenge obtained from administering a challenge virus (virulent IBDV strain variant-E), 14 days after vaccination. Presence of IBDV in the bursa of Fabricius and microscopic lesions in the bursa of 5–15 animals per group were investigated, 3 and 14 days after vaccination and 3 and 10 days after challenge. Protection against challenge was determined. Furthermore, the serological response against classical and variant E viruses was determined with the VN-test, 14 days after vaccination.

Experiment 2

In a second potency test the effect of the vaccine was assessed by measurement of the serological response and resistance to challenge obtained from administering a challenge virus 14 days after administering the Gumboro vaccine strain classical/variant E (TC)-254(Gly)/270(Thr) via the eye drop route.

Fourteen days old chickens were divided in 3 groups. One group was vaccinated with classical/variant E (TC)-254(Gly)/270(Thr) (P9), one group with original classical/variant E (TC)-254(Gly)/270(Thr) (P3) and the last group with commercial vaccine Nobilis Gumboro D78.

At 3, 7 and 14 days after the vaccination, bursa's were taken from 3–15 chickens per group. The bursa's were examined for lesions and the presence of viral antigen. Fourteen days after the vaccination four non-vaccinated SPF chickens of the same age and source were added to each group. Blood was taken from all animals and all animals were challenged with virulent IBDV strain F52/70 via the eye drop route. For a period of 10 days clinical signs and mortality were scored. At three days after challenge, bursa's were isolated from 5 chickens per group. The bursa's were examined for lesions and the presence of viral antigen. At ten days after challenge, bursa's from the surviving animals were examined for the presence of microscopic lesions.

Results

Experiment 1

(i) Average Microscopic Lesion Score in the Bursa 3 and 14 Days After Vaccination and 3 and 10 Days After Challenge Results are depicted in table 4. The none-vaccinated control-animals were not protected, the challenge virus induced acute lesions and complete lymphocytic depletion, 3 and 10 days after challenge. In contrast the broadspectrum vaccine classical/variant E (TC)-254(Gly)/270(Thr) did induce only mild to moderate lesions after vaccination. Furthermore, 3 days after challenge only mild to moderate chronic lesions were observed indicating that the animals were protected against challenge with virulent variant E IBDV. Ten days after challenge the lesions in the vaccinated group diminished further.

TABLE 4

Average bursal lesion score of classical/variant E (TC)-254(Gly)/270(Thr) (P3).

| Route | Dose | Days after vaccination | | Days after challenge | |
|---|---|---|---|---|---|
| | | 3 | 14 | 3 | 10 |
| ED | 2.7 | 0 | 3.6 | 3.0C | 2.3 |
| ED | 3.7 | 2.8 | 3.4 | 4.0C | 1.5 |
| ED | 4.7 | 2.6 | 2.8 | 3.0C | 1.9 |
| IM | 2.5 | 0 | 2.2 | 1.6C | 1.4 |
| IM | 3.5 | 0 | 3.2 | 1.0C | 1.0 |
| IM | 4.5 | 0.8 | 1.8 | 2.0C | 1.3 |
| None vaccinated controls | | | | 5.0A | 5.0 |

ED = Eye-drop route;
(IM) = intramuscular route;
C = chronic lesions;
A = acute lesions (ii) Serological Response Against IBDV As VN-IBDV-viruses were used a classical and a variant-E strain. It can be seen in table 5, that classical/variant E (TC)-254(Gly)/270(Thr) (P3) induced a good serological response against classical as well as variant E strains of IBDV indicating the broadspectrum nature of the virus.

TABLE 5

Serological response 14 days after vaccination
(VN-titre is expressed as log2 of the dilution).

| Route | Dose | classical VN virus | Variant-E VN virus |
|---|---|---|---|
| ED | 2.7 | 8.2 ± 1.3 | 8.3 ± 1.1 |
| ED | 3.7 | 8.0 ± 1.4 | 7.7 ± 1.5 |
| ED | 4.7 | 7.6 ± 1.4 | 8.0 ± 1.7 |
| IM | 2.5 | 7.6 ± 1.1 | 7.4 ± 1.8 |
| IM | 3.5 | 7.5 ± 1.7 | 7.2 ± 2.0 |
| IM | 4.5 | 8.1 ± 0.9 | 7.1 ± 1.4 |
| None vaccinated controls | | <4.0 ± 0.0 | <4.0 ± 0.0 |

ED = Eye-drop route;
(IM) = intramuscular route.
(iii) Detection of IBDV with an ELISA system in the bursa 3 and 14 days after vaccination and 3 days after challenge.

(iii) Detection of IBDV with an ELISA System in the Bursa 3 and 14 days After Vaccination and 3 Days After Challenge As can be seen from table 6, virus could be isolated 3 days after vaccination in animals vaccinated with the higher doses. No virus could be detected in any of the vaccinated animals 3 days after challenge indicating that all animals were protected against challenge. In contrast, all control animals contained viral antigen in the bursa after challenge.

TABLE 6

Presence of IBDV in the bursa of Fabricius.

| Route | Dose | Days after vaccination | | Days after challenge | |
|---|---|---|---|---|---|
| | | 3 | 14 | 3 | % protection |
| ED | 2.7 | 0/5* | 15 | 0/5 | 100 |
| ED | 3.7 | 4/5 | 0/5 | 0/5 | 100 |
| ED | 4.7 | 3/5 | 0/5 | 0/5 | 100 |
| IM | 2.5 | 0/5 | 0/5 | 0/5 | 100 |
| IM | 3.5 | 0/5 | 0/5 | 0/5 | 100 |

TABLE 6-continued

Presence of IBDV in the bursa of Fabricius.

| Route | Dose | Days after vaccination | | Days after challenge | |
|---|---|---|---|---|---|
| | | 3 | 14 | 3 | % protection |
| IM | 4.5 | 2/5 | 0/5 | 0/5 | 100 |
| None vaccinated controls | | | | 12/12 | 0 |

ED = Eye-drop route;
(IM) = intramuscular route;
*Number of positive animals with viral antigen present per total number investigated Experiment 2

(i) Average Microscopic Lesion Score in the Bursa 3 and 14 Days After Vaccination and 3 and 10 Days After Challenge As can be seen from table 7, the none-vaccinated control-animals were not protected and the challenge virus induced complete lymphocytic depletion, 3 and 10 days after challenge yielding acute lesions after challenge. In contrast the broadspectrum vaccine classical/variant E (TC)-254(Gly)/270(Thr) did induce mild to moderate lesions after vaccination. Furthermore, 3 days after challenge mild to moderate chronic lesions were observed indicating that the animals were protected against challenge with classical virulent IBDV strain F52/70. In the group vaccinated with classical/variant E (TC)-254(Gly)/270(Thr) P9, one animal showed severe acute lesions, 3 days after challenge, indicating that it was not protected. Ten days after challenge the lesions in the bursa of animals vaccinated with classical/variant E (TC)-254(Gly)/270(Thr) further diminished and were all of a mild to moderate nature, indicting that all investigated animals were protected.

TABLE 7

Average bursal lesion score of Nobilis Gumboro D78 and the classical/variant E (TC)-254(Gly)/270(Thr) strain at passage level 3 or 9.

| Vaccine | Dose | Protection (%) | Days after vaccination | | Days after challenge | |
|---|---|---|---|---|---|---|
| | | | 3 | 14 | 3 | 10 |
| Passage 9 | 3.6 | 95 | 2.8 | 4.3 | 3.3 | 1.9 |
| Passage 3 | 4.1 | 100 | 2.6 | 4.0 | 3.5 | 2.3 |
| Nobilis D78 | 5.1 | 74 | 0 | 3.3 | 2.5 | 2.5 |
| None vaccinated controls | | 0 | | | 5.0 | 5.0 |

(ii) Serological Response Against IBDV

As VN-IBDV-viruses were used a classical and a variant-E strain. It can be seen in table 8, that classical/variant E (TC)-254(Gly)/270(Thr) (P3 and P9) induced a good serological response against classical as well as variant-E strains of IBDV indicating the broadspectrum nature of the virus. In contrast the group vaccinated with D78 (dose 5.1 log10) induced an average serological response against classical- and variant E virus of 8.8 log2 and 5.9 log2, respectively, clearly demonstrating the classical nature of this vaccine.

TABLE 8

Serological response 14 days after vaccination

| Vaccine | Dose | classical VN virus | Variant-E VN virus |
|---|---|---|---|
| Passage 9 | 3.6 | 7.3 ± 1.8 | 7.3 ± 1.5 |
| Passage 3 | 4.1 | 8.4 ± 1.7 | 7.8 ± 1.8 |
| D78 | 5.1 | 8.8 ± 3.4 | 5.9 ± 1.8 |
| None vaccinated controls | | <4.0 ± 0.0 | <4.0 ± 0.0 |

(VN-titre is expressed as log2 of the dilution).

(iii) Detection of IBDV an ELISA System in the Bursa 3, 7 and 14 Days After Vaccination and 3 Days After Challenge As can be seen from table 9, virus could be isolated 3–14 days after vaccination. Virus could only be detected in one animal vaccinated with classical/variant E (TC)-254(Gly)/270(Thr) passage 9, 3 days after challenge indicating that this animal was not protected against challenge. All other animals were protected against challenge

TABLE 9

Presence of IBDV in the bursa of Fabricius.

| Vaccine | Dose | Days after vaccination | | | Days after challenge | |
|---|---|---|---|---|---|---|
| | | 3 | 7 | 14 | 3 | % protection |
| Passage 9 | 3.6 | 0/5* | 2/3 | 0/3 | 1/4 | 75 |
| Passage 3 | 4.1 | 0/5 | 2/3 | 0/3 | 0/4 | 100 |
| D78 | 5.1 | 1/5 | 2/3 | 1/3 | 0/4 | 100 |
| None vaccinated controls | | | | | 9/9 | 0 |

*Number of positive animals with viral antigen present per total number investigated Example 3

Safety and Efficacy of Broad Spectrum IBDV Mutants

Material and Methods

A further animal experiment was carried out to investigate the safety and efficacy characteristics of different broadspectrum vaccine virus strains. The broadspectrum virus strains varied in segment B being derived from Gumboro virus strain D78 or P2. Furthermore, Gumboro strains, in which only one of the 2 changes (at positions 254 and 270) in segment A were introduced, were investigated. In this experiment the effect of the vaccine was assessed by measurement of the serological response and resistance to challenge obtained from administering a challenge virus (F52/70), 14 days after administering the Gumboro vaccine strains. The vaccines investigated were the broadspectrum vaccine virus strains:

classical/variant E (TC)-254(Gly)/270(Thr)//D78B classical/variant E (TC)-254(Gly)/270(Thr)//P2B classical/variant E (TC)-254(Gly)//D78B classical/variant E (TC)-254(Gly)//P2B classical/variant E (TC)-270(Thr)//D78B classical/variant E (TC)-270 (Thr)//P2B.

The different broadspectrum vaccines at a dose between $10^{3.4}$ and $10^{4.8}$ TCID$_{50}$/animal, were applied via the eye-drop route at 3 weeks of age. Presence of IBDV in the bursa of Fabricius and microscopic lesions in the bursa of 5 animals per group were investigated, 3 and 14 days after vaccination and 3 and/or 10 days after challenge. Protection against challenge was determined. Furthermore, the serological response against classical and variant-E viruses was determined with the VN-test, 14 days after vaccination.

Results (i) Average Microscopic Lesion Score and Detection of IBDV-antigen in the Bursa Results are shown in tables 10 and 11. All IBDV mutants display a reduced virulence. The mutants having a segment B of strain D78 induce moderate lesions, whereas the attenuated properties of the mutants having a segment B of strain P2 display even milder properties. classical/variant E (TC)-254(Gly)/270(Thr)//D78B resulted in 40% protection. The other strains induced complete protection, 3 days after challenge (only chronic lesions present), except for classical/variant E (TC)-270 (Thr)//P2B that was not effective after eye-drop administration. All other groups showed mild to moderate lesions, 10 days after challenge.

TABLE 10

Average bursal lesion score

| Virus | Days after vaccination | | Days after challenge | |
|---|---|---|---|---|
| | 3 | 14 | 3 | 10 |
| classical/variant E (TC)-254(Gly)/270(Thr)//D78B | 0.0 | 3.4 | 3.6A/C | 1.5 |
| classical/variant E(TC)-254(Gly)//D78B | 0.0 | 3.0 | 3.8C | 2.7 |
| classical/variant E (TC)-270(Thr)//D78B | 0.4 | 4.2 | 4.6C | 3.0 |
| classical/variant E (TC)-254(Gly)/270(Thr)//P2B | 0.8 | 2.0 | 1.4C | 1.5 |
| classical/variant E (TC)-254(Gly)//P2B | 0.8 | 2.0 | 2.6C | 1.6 |
| classical/variant E (TC)-270 (Thr)//P2B | 0.0 | 0.0 | 5.0A | 5.0 |
| None vaccinated controls | ND | 0.0 | 5.0A | 5.0 |

C = chronic lesions;
A = acute lesions

TABLE 11

Presence of IBDV in the bursa of Fabricius.

| Virus | Days after vaccination | | Days after challenge | |
|---|---|---|---|---|
| | 3 | 14 | 3 | % protection |
| classical/variant E (TC)-254(Gly)/270(Thr)//D78B | 0/5* | 0/5 | 3/5 | 40 |
| classical/variant E (TC)-254(Gly)//D78B | 0/5 | 0/5 | 0/5 | 100 |
| classical/variant E (TC)-270(Thr)//D78B | 0/5 | 0/5 | 0/5 | 100 |
| classical/variant E (TC)-254(Gly)/270(Thr)//P2B | 2/5 | 0/5 | 0/5 | 100 |
| classical/variant E (TC)-254(Gly)//P2B | 1/5 | 0/5 | 0/5 | 100 |
| classical/variant E (TC)-270 (Thr)//P2B | 0/5 | 0/5 | 8/8 | 0 |
| None vaccinated controls | ND | ND | 13/13 | 0 |

*Number of positive animals with viral antigen present per total number investigated.

(ii) Serological Response Against IBDV

A classical and a variant-E strain were used as VN-IBDV viruses. It can be seen in table 12, that the IBDV vaccine strains induced a good serological response against classical as well as variant-E strains of IBDV. The classical/variant E (TC)-270 (Thr)//P2B mutant did not take after eye-drop administration of the virus.

TABLE 12

Serological response, 14 days after vaccination (VN-titres are expressed as log2 of the dilution). x = 4 out of 25 did not respond, y = 1 out of 25 did not respond, z = 2 out of 25 did not respond.

| Virus | Classical VN virus | Variant-E VN virus |
|---|---|---|
| classical/variant E (TC)-254(Gly)/270(Thr)//D78B | 7.9 ± 2.2$^x$ | 6.5 ± 1.9$^x$ |
| classical/variant E (TC)-254(Gly)//D78B | 8.0 ± 1.5$^y$ | 8.2 ± 1.4 |
| classical/variant E (TC)-270(Thr)//D78B | 9.0 ± 1.6$^y$ | 8.8 ± 1.4 |
| classical/variant E (TC)-254(Gly)/270(Thr)//P2B | 7.7 ± 1.6$^y$ | 6.7 ± 1.5$^z$ |
| classical/variant E (TC)-254(Gly)/P2B | 7.5 ± 1.8$^z$ | 6.8 ± 1.7$^y$ |
| classical/variant E (TC)-270(Thr)//P2B | <4.0 ± 0.0 | <4.0 ± 0.0 |
| None vaccinated controls | <4.0 ± 0.0 | <4.0 ± 0.0 |

LEGENDS TO THE FIGURES

FIG. 1.

Construction of chimeric cDNA clones of segment A of IBDV. A map of the genomic organization of the IBDV segment A is shown at the top of the figure. Coding sequences of segment A of strain D78 are depicted by an open box. E/Del sequences are marked by shaded boxes. Location of mutated amino acids are indicated and named by single letter code. Numbering of nucleotides and amino acids are according to the published sequence of strain P2 (Mundt and Müller, 1995, supra). nt, nucleotides

FIG. 2.

Construction of chimeric cDNA clones of segment A of IBDV. A map of the genomic organization of the IBDV segment A is shown at the top of the figure. Coding sequences of segment A of the chimeric cDNA clone pD78A-E/DelMut12 are depicted by an open box. Sequences of the chimeric cDNA clone pD78A-E/Del-QH-AT (Mundt, 1999, supra) are marked by black boxes. Restriction enzymes and their cleavage sites used for cloning are indicated. Location of mutated amino acids are indicated and named by single letter code. Numbering of nucleotides and amino acids are according to the published sequence of strain P2 (Mundt and Müller, 1995, supra). nt, nucleotides

What is claimed is:

1. An IBDV mutant comprising nucleotide sequences encoding a variant E VP2 protein in segment A of the viral genome thereof that is capable of infecting and replicating in chicken embryo fibroblast tissue culture (CEF), said mutant comprising one or more mutations in the variant E VP2 coding region such that,
   (i) the codon for the amino acid at position 254 encodes Glycine, and/or
   (ii) the codon for the amino acid at position 270 encodes Threonine.

2. The mutant according to claim 1, wherein the codon for amino acid 254 is GGC and/or the codon for amino acid 270 is ACG.

3. A mutant IBDV comprising nucleotide sequences encoding a variant E VP2 protein in segment A of the viral genome thereof that is capable of infecting and replicating in chicken embryo fibroblast (CEF) tissue culture, wherein the coding region for the 253–284 fragment of the variant E VP2 protein is replaced by the corresponding coding region of IBDV strain D78.

4. The mutant according to claim 1, wherein the backbone of segment A is of an IBDV of a classical subtype.

5. The mutant according to claim 1, wherein segment B of the viral genome thereof is of a classical IBDV subtype.

6. A vaccine for use in the protection of poultry against disease caused by IBDV infection, comprising an effective amount of an IBDV mutant according to claim 1 for providing protection against classical and variant E subtypes together with a pharmaceutically acceptable carrier or diluent.

7. The vaccine according to claim 6, wherein the IBDV mutant is in a live form.

8. A method for the protection of poultry against disease caused by IBDV infection, comprising administering an effective amount of the vaccine according to claim 6 for providing protection against classical and variant E subtypes.

9. A method according to claim 8, wherein the vaccine is administered via a mass application route.

10. The method of claim 8, wherein the IBDV mutant in the vaccine is in a live form.

11. The mutant according to claim 3, wherein the backbone of segment A is of an IBDV of a classical subtype.

12. The mutant according to claim 4, wherein the backbone of segment A is of strain D78.

13. The mutant according to claim 11, wherein the backbone of segment A is of strain D78.

14. The mutant according to claim 5, wherein segment B of the viral genome is of strain D78.

15. The mutant according to claim 11, wherein segment B of the viral genome is of strain D78.

* * * * *